(12) United States Patent
Rapoport

(10) Patent No.: US 9,709,652 B2
(45) Date of Patent: Jul. 18, 2017

(54) MRI SYSTEM WITH MEANS TO ELIMINATE OBJECT MOVEMENT WHILST ACQUIRING ITS IMAGE

(71) Applicant: Aspect Imaging Ltd., Shoham (IL)

(72) Inventor: Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 140 days.

(21) Appl. No.: 13/939,338

(22) Filed: Jul. 11, 2013

(65) Prior Publication Data

US 2014/0099010 A1 Apr. 10, 2014

Related U.S. Application Data

(60) Provisional application No. 61/710,725, filed on Oct. 7, 2012.

(51) Int. Cl.
| | | |
|---|---|---|
| G06K 9/00 | (2006.01) | |
| G01R 33/565 | (2006.01) | |
| A61B 5/00 | (2006.01) | |
| G06T 7/00 | (2017.01) | |
| G01R 33/563 | (2006.01) | |

(52) U.S. Cl.
CPC ...... *G01R 33/56509* (2013.01); *G06T 7/0012* (2013.01); *A61B 5/0033* (2013.01); *G01R 33/56308* (2013.01); *G06T 7/0014* (2013.01)

(58) Field of Classification Search
None
See application file for complete search history.

(56) References Cited

U.S. PATENT DOCUMENTS

| 5,427,101 A * | 6/1995 | Sachs ................ G01R 33/5676 |
| | | 324/309 |
| 5,602,891 A | 2/1997 | Pearlman |
| 8,807,084 B2 | 8/2014 | Rapoport et al. |
| 8,851,018 B2 | 10/2014 | Rapoport et al. |
| 8,896,310 B2 | 11/2014 | Rapoport |
| 2004/0171927 A1 | 9/2004 | Lowen et al. |

(Continued)

FOREIGN PATENT DOCUMENTS

| WO | 2007136745 A2 | 11/2007 |
| WO | WO 2011127942 A1 * | 10/2011 |

OTHER PUBLICATIONS

J. Barral et al. "Real-Time Motion Correction for High-Resolution Larynx Imaging," Magn Reson Med. Jul. 2011 ; 66(1): 174-179.*

(Continued)

*Primary Examiner* — Vu Le
*Assistant Examiner* — Samah Beg
(74) *Attorney, Agent, or Firm* — Pearl Cohen Zedek Latzer Baratz LLP

(57) ABSTRACT

A method of reducing the effect of object movements along MRI imaging. The method includes: acquiring a sequence of MRI consecutive images of an object; storing on a computer readable medium, for each of the images, at least one parameter p indicating spatial image orientation at which the image was taken; analyzing the sequence of the images for detection of the object movement; and tagging images of at least one movement of the object.

19 Claims, 3 Drawing Sheets

(56) References Cited

U.S. PATENT DOCUMENTS

| | | | |
|---|---|---|---|
| 2005/0033123 A1* | 2/2005 | Gardner | G06T 7/0016 600/300 |
| 2006/0079754 A1 | 4/2006 | Welch et al. | |
| 2007/0249929 A1* | 10/2007 | Jeong | G01R 33/5615 600/410 |
| 2009/0092305 A1* | 4/2009 | Ditt et al. | 382/131 |
| 2011/0162652 A1 | 7/2011 | Rapoport | |
| 2011/0186049 A1 | 8/2011 | Rapoport | |
| 2011/0201916 A1 | 8/2011 | Duyn et al. | |
| 2011/0221439 A1* | 9/2011 | Posse | 324/307 |
| 2011/0230755 A1* | 9/2011 | MacFarlane et al. | 600/414 |
| 2011/0234347 A1 | 9/2011 | Rapoport | |
| 2011/0304333 A1 | 12/2011 | Rapoport | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0119742 A1 | 5/2012 | Rapoport | |
| 2012/0243756 A1 | 9/2012 | Samsonov et al. | |
| 2013/0079624 A1 | 3/2013 | Rapoport | |
| 2013/0093866 A1* | 4/2013 | Ohlhues et al. | 348/65 |
| 2013/0109956 A1 | 5/2013 | Rapoport | |
| 2013/0229177 A1* | 9/2013 | Bammer | G01R 33/56341 324/309 |
| 2013/0237803 A1 | 9/2013 | Rapoport | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0103927 A1 | 4/2014 | Rapoport | |
| 2014/0117989 A1 | 5/2014 | Rapoport | |
| 2014/0128725 A1 | 5/2014 | Rapoport et al. | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0171784 A1* | 6/2014 | Ooi et al. | 600/414 |
| 2014/0219531 A1* | 8/2014 | Epstein | G01R 33/56308 382/131 |
| 2014/0230850 A1 | 8/2014 | Rapoport | |
| 2014/0257081 A1 | 9/2014 | Rapoport | |
| 2014/0266203 A1 | 9/2014 | Rapoport et al. | |
| 2014/0275966 A1* | 9/2014 | Schwartz et al. | 600/411 |
| 2014/0300358 A1 | 10/2014 | Rapoport | |
| 2014/0378821 A1 | 12/2014 | Rapoport et al. | |
| 2014/0378825 A1 | 12/2014 | Rapoport et al. | |
| 2015/0059655 A1 | 3/2015 | Rapoport | |
| 2015/0065788 A1 | 3/2015 | Rapoport | |
| 2015/0066413 A1* | 3/2015 | Bhagat | G01R 33/3692 702/104 |
| 2015/0257675 A1* | 9/2015 | Bottomley | G01R 33/34084 600/423 |
| 2015/0265219 A1* | 9/2015 | Feiweier | A61B 5/721 600/476 |
| 2016/0077180 A1* | 3/2016 | Beck | G01R 33/567 324/309 |

OTHER PUBLICATIONS

J.G. Pipe. "Motion Correction With PROPELLER MRI: Application to Head Motion and Free-Breathing Cardiac Imaging," Magnetic Resonance in Medicine 42:963-969 (1999).*

T. Brown et al. "Prospective motion correction of high-resolution magnetic resonance imaging data in children," NeuroImage 53 (2010) 139-145.*

Alhamud, A., Tisdall, M. D., Hess, A. T., Hasan, K. M., Meintjes, E. M., & van der Kouwe, A. J. (2012). Volumetric navigators for real-time motion correction in diffusion tensor imaging. Magnetic resonance in medicine,68(4), 1097-1108.*

Frost, R., Hess, A. T., Okell, T. W., Chappell, M. A., Tisdall, M. D., van der Kouwe, A. J., & Jezzard, P. (2015). Prospective motion correction and selective reacquisition using volumetric navigators for vessel-encoded arterial spin labeling dynamic angiography. Magnetic resonance in medicine.*

Singh, A., Zahneisen, B., Keating, B., Herbst, M., Chang, L., Zaitsev, M., & Ernst, T. (2015). Optical tracking with two markers for robust prospective motion correction for brain imaging. Magnetic Resonance Materials in Physics, Biology and Medicine, 28(6), 523-534.*

White, N., Roddey, C., Shankaranarayanan, A., Han, E., Rettmann, D., Santos, J., . . . & Dale, A. (2010). PROMO: Real-time prospective motion correction in MRI using image-based tracking. Magnetic Resonance in Medicine, 63(1), 91-105.*

Ooi, M. B., Krueger, S., Thomas, W. J., Swaminathan, S. V., & Brown, T. R. (2009). Prospective real-time correction for arbitrary head motion using active markers. Magnetic resonance in medicine, 62(4), 943-954.*

Forman, C., Aksoy, M., Hornegger, J., & Bammer, R. (2011). Self-encoded marker for optical prospective head motion correction in MRI. Medical image analysis, 15(5), 708-719.*

Aksoy, M., Forman, C., Straka, M., Skare, S., Holdsworth, S., Hornegger, J., & Bammer, R. (2011). Real-time optical motion correction for diffusion tensor imaging. Magnetic resonance in medicine, 66(2), 366-378.*

Andrews-Shigaki, B. C., Armstrong, B. S., Zaitsev, M., & Ernst, T. (2011). Prospective motion correction for magnetic resonance spectroscopy using single camera retro-grate reflector optical tracking. Journal of Magnetic Resonance Imaging, 33(2), 498-504.*

Qin, L., van Gelderen, P., Derbyshire, J. A., Jin, F., Lee, J., de Zwart, J. A., . . . & Duyn, J. H. (2009). Prospective head-movement correction for high-resolution MRI using an in-bore optical tracking system. Magnetic resonance in medicine, 62(4), 924-934.*

Speck, O., Hennig, J., & Zaitsev, M. (2006). Prospective real-time slice-by-slice motion correction for fMRI in freely moving subjects. Magnetic Resonance Materials in Physics, Biology and Medicine, 19(2), 55-61.*

Aspect Imaging Ltd, "MRI—Incubator's Closure Assembly", co-pending U.S. Appl. No. 14/539,442, filed Nov. 12, 2014.

Aspect Imaging Ltd., "Shutting Assembly for Closing an Entrance of an MRI Device", co-pending U.S. Appl. No. 14/540,163, filed Nov. 13, 2014.

Aspect Imaging Ltd., "Cage in an MRD with a Fastening/Attenuating System", co-pending U.S. Appl. No. 14/527,950, filed Oct. 30, 2014.

Rapoport, Uri, "RF Shielding Conduit in an MRI Closure Assembly", co-pending U.S. Appl. No. 14/574,785, filed Dec. 18, 2014.

Aspect Imaging Ltd., "System and Method for Generating Invasively Hyperpolarized Images", co-pending U.S. Appl. No. 14/556,682, filed Dec. 1, 2014.

Aspect Imaging Ltd., "System and Method for Generating Invasively Hyperpolarized Images", co-pending U.S. Appl. No. 14/556,654, filed Dec. 1, 2014.

Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.

Aspect Imaging Ltd., "Means for Operating an MRI Device Within a RF-Magnetic Environment", co-pending U.S. Appl. No. 14/596,320, filed Jan. 14, 2015.

Aspect Imaging Ltd., "Means and Method for Operating an MRI Device Within a RF-Magnetic Environment", co pending U.S. Appl. No. 14/596,329, filed Jan. 14, 2015.

Aspect Imaging Ltd., "CT/MRI Integrated System for the Diagnosis of Acute Strokes and Methods Thereof", co pending U.S. Appl. No. 14/598,517, filed Jan. 16, 2015.

Aspect Imaging Ltd., "RF Automated Tuning System Used in a Magnetic Resonance Device and Methods Thereof", co-pending U.S. Appl. No. 14/588,741, filed Jan. 2, 2015.

Aspect Imaging Ltd., "A Method for Providing High Resolution, High Contrast Fused MRI Images", co-pending U.S. Appl. No. 13/877,553, filed Apr. 3, 2013.

(56) References Cited

OTHER PUBLICATIONS

Aspect Imaging Ltd., "A Method for Manipulating the MRI's Protocol of Pulse-Sequences", co-pending U.S. Appl. No. 14/070,695, filed Nov. 4, 2013.
Extended European Search Report issued by the European Patent Office dated Jun. 2, 2014 in corresponding European Application No. 13187323.4-1560.
Sachs et al., Real-Time Motion Detection in Spiral MRI Using Navigators, the Information Systems Laboratory, Department of Electrical Engineering, Stanford University Stanford, California, Jul. 1994, pp. 639-645, MRM 32, USA.
Zaitsev et al., Magnetic resonance imaging of freely moving objects: real-time motion correction using an external optical motion tracking system, NeuroImage, Jul. 1, 2006, pp. 1038-1050, vol. 31, Issue 3, Freiburg, Germany.
Zoroofi, et al., "MRI artifact cancellation due to rigid motion in the imaging plane", Medical Imagining, IEEE Transactions on Medical Imaging, Dec. 1996, pp. 768-784, vol. 15, Issue 6, Osaka University, Japan.
Ranieri, Shawn Michael, "Development of Simulator Training to Reduce Head Motion Artifact in fMRI", Thesis—Institute of Biomaterials and Biomedical Engineering University of Toronto, 60 pages, 2011, Toronto, Canada.
Aspect Imaging Ltd., "Foamed Patient Transport Incubator", co-pending U.S. Appl. No. 14/531,289, filed Nov. 3, 2014.
Aspect Imaging Ltd., "Mechanical Clutch for MRI", co-pending U.S. Appl. No. 14/611,379, filed Feb. 2, 2015.
Aspect Imaging Ltd., "Incubator Deployable Multi-Functional Panel", co-pending U.S. Appl. No. 14/619,557, filed Feb. 11, 2015.
Aspect Imaging Ltd., "MRI Thermo-Isolating Jacket", co-pending U.S. Appl. No. 14/623,039, filed Feb. 16, 2015.
Aspect Imaging Ltd., "MRI RF Shielding Jacket", co-pending U.S. Appl. No. 14/623,051, filed Feb. 16, 2015.
Aspect Imaging Ltd., "Capsule for a Pneumatic Sample Feedway", co-pending U.S. Appl. No. 14/626,391, filed Feb. 19, 2015.
Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.
Aspect Imaging Ltd., "Temperature-Controlled Exchangeable NMR Probe Cassette and Methods Thereof", co pending U.S. Appl. No. 14/504,890, filed Oct. 2, 2014.
Aspect Imaging Ltd., "NMR Extractable Probe Cassette Means and Methods Thereof", co-pending U.S. Appl. No. 14/504,907, filed Oct. 2, 2014.

* cited by examiner

MRI SYSTEM WITH MEANS TO ELIMINATE OBJECT MOVEMENT WHILST ACQUIRING ITS IMAGE

CROSS-REFERENCE TO RELATED APPLICATIONS

This application claims priority from U.S. Provisional Patent Application No. 61/710,725, filed Oct. 7, 2012, which is incorporated herein by reference in its entirety.

FIELD OF THE INVENTION

The present invention pertains to means and methods for reducing the effect of object movements along MRI imaging.

BACKGROUND OF THE INVENTION

Subject motion and associated artifacts limit the applicability of magnetic resonance imaging (MRI) and the achievable quality of the images acquired, See Zaitsev et al., Magnetic resonance imaging of freely moving objects: prospective real-time motion correction using an external optical motion tracking system, *NeuroImage* 31(3), 1038-1050 (2006). Post-processing techniques have been developed to suppress MRI artifact arising from object planar rigid motion, See for example Zoroofi et al., *IEEE Transaction on Medical Imaging*, 15(6), 768-784 (1996). More over, a few patents, such as U.S. Pat. No. 5,602,891 disclose computerized tomography (CT) scanners & functional MRI (fMRI) imaging apparatus with means for compensation object motion.

As presented by Ranieri (2011), during fMRI acquisition, light restraints (i.e. foam wedges, vacuum pillows, straps, etc.) are used to help limit head motion. These restraints are most effective in restricting motion in the medial-lateral direction, and less effective for motion in orthogonal directions. With the desire to keep patient discomfort and stress at a minimum, head restraint is only lightly used and is not an extremely effective technique for preventing motion in fMRI, See Ranieri, S. M., "Development of Simulator Training to Reduce Head Motion Artifact in fMRI", Master's Thesis in Health Science, Institute of Biomaterials and Biomedical Engineering, University of Toronto, 2011.

Hence, MRI devices targeted for avoiding motion artifacts and specialized in producing an image sequence with reduced object-movement affect, and especially such as MRI systems adapted to image uncontrollably movable objects, such as neonates, premature babies and laboratory animals; and especially in those special cases were restrain is to be avoided, is still a long felt and unmet need.

SUMMARY OF THE INVENTION

It is thus an object of the current invention to disclose a first method for avoiding object motion artifacts along MRI imaging. The method comprising steps of: (a) acquiring a sequence of N MRI consecutive images $CI_n$ of an object; (b) storing on a computer readable medium (CRM) for each of said $CI_n$: at least one parameter p indicating spatial image orientation at which said image was taken; (c) analyzing said sequence of said $CI_n$ for detection of said object movement; and tagging thereby $K_M$ images $CI_k^M$ of at least one movement M of said object; (d) for each of said movement M, determining the following using said tagged images $CI_k^M$: two of the following: the movement starting time $T_{MS}$, the movement ending time $T_{ME}$, and time length of said movement $T_M$; the movement spatial image orientation parameter $P_{MS}$ at the beginning of the movement, wherein said method additionally comprising for each said M, whose $T_M$ is shorter from a predetermined time length PT, steps of (e) acquiring a sequence of $K_M$ MRI consecutive images $NCI_k^M$ starting at said $P_{MS}$; and ending after said $T_M$; (f) replacing said $CI_k^M$ with said $NCI_k^M$, then replacing, in said sequence $CI_n$, the images that correspond in location to $CI_k^M$ with its respective $CI_k^M$ image; (g) repeating steps (c)-(f) until no more movements whose $T_M$ is shorter than said PT can be detected; thereby, producing an image sequence with reduced object-movement in MRI imaging. The method hence enhanced the quality of the MRI images acquired, increases SNR and decreases associated artifacts.

It is another object of the current invention to disclose a second method for reducing the effect of object movements along MRI imaging; the method comprising steps of: (a) acquiring a sequence of N MRI consecutive images $CI_n$ of an object; (b) storing on a computer readable medium (CRM) for each of said $CI_n$: at least one parameter p indicating spatial image orientation at which said image was taken; by means of one or more non-MRI motion detectors, (c) analyzing motion of said object and tagging thereby $K_M$ images $CI_k^M$ of at least one movement M of said object; (d) for each of said movement M, determining the following using said tagged images $CI_k^M$: two of the following: the movement starting time $T_{MS}$, the movement ending time $T_{ME}$, and time length of said movement $T_M$; the movement spatial image orientation parameter $P_{MS}$ at the beginning of the movement, wherein said method additionally comprising for each said M, whose $T_M$ is shorter from a predetermined time length PT, steps of (e) acquiring a sequence of $K_M$ MRI consecutive images $NCI_k^M$ starting at said $P_{MS}$; and ending after said $T_M$; replacing said $CI_k^M$ with said $NCI_k^M$, then (f) replacing, in said sequence $CI_n$, the images that correspond in location to $CI_k^M$ with its respective $CI_k^M$ image; (g) repeating steps (c)-(f) until no more movements whose $T_M$ is shorter than said PT can be detected; thereby, producing an image sequence with reduced object-movement in MRI imaging.

It is another object of the current invention to disclose a method for reducing the effect of object movements along MRI imaging as defined in any of the above, additionally comprising a step of selecting the non-MRI motion detectors from a group consisting of or otherwise comprising: passive infrared sensors; detectors which senses body heat; mechanical detector; electronic detectors; optical detectors; acoustical detectors; sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

It is another object of the current invention to disclose a method as defined in any of the above, wherein the method additionally comprising step of selecting said parameter from a group consisting of: angel of image with respect to the object, spatial coordinates of the area of the image, location of MRI components and a combination thereof.

It is another object of the current invention to disclose a method as defined in any of the above, wherein the method additionally comprising step of selecting said object from a group consisting of: adult person, person under anesthesia, infant, premature baby, animal and a combination thereof.

It is another object of the current invention to disclose a method as defined in any of the above, wherein the method additionally comprising step of characterizing at least one of said movement M by the extent of said movement.

It is another object of the current invention to disclose a method as defined in any of the above, wherein the method additionally comprising an image processing step prior to step (c); wherein said processing step comprising performing Fourier transformation on said consecutive image to momentum space (K-space).

It is another object of the current invention to disclose a method as defined in any of the above, wherein said step of analyzing is performed on images in K-space.

It is another object of the current invention to disclose an MRI system imaging a movable object. The MRI system comprising: an MRI device adapted to take a sequence of N MRI consecutive images $CI_n$ of an object; each of said images is characterized by at least one parameter p indicating spatial image orientation at which said image was taken; a computer readable medium (CRM) in communication with said MRI; said CRM having instructions thereon for executing a method comprising steps of: analyzing said sequence of said $CI_n$; and tagging thereby $K_M$ images $CI_k^M$ of at least one movement M of said object; for each of said movement M, determining the following using said tagged images $CI_k^M$: (a) two of the following: the movement starting time $T_{MS}$, the movement ending time $T_{ME}$, and time length of said movement $T_M$; and (b) the movement spatial image orientation parameter $P_{MS}$ at the beginning of the movement; wherein for each said M, whose $T_M$ is shorter from a predetermined time length PT, said instructions are additionally adapted for acquiring a sequence of $K_M$ MRI consecutive images $NCI_k^M$ starting at said $P_{MS}$; and ending after said $T_M$; replacing said $CI_k^M$ with said $NCI_k^M$, then replacing said sequence $CI_n$ the images that correspond in location to $CI_k^M$ with its respective $CI_k^M$ image; and repeating steps (i)-(iv) until no more movements whose $T_M$ is shorter from said PT can be detected.

It is another object of the current invention to disclose an MRI system imaging a movable object as defined above, wherein said MRI system additionally comprising a non-MRI motion detectors.

It is another object of the current invention to disclose an MRI system imaging a movable object as defined in any of the above, wherein the non-MRI motion detectors are selected from a group consisting of or otherwise comprising: passive infrared sensors; detectors which senses body heat; mechanical detector; electronic detectors; optical detectors; acoustical detectors; sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

It is another object of the current invention to disclose an MRI system imaging a movable object as defined in any of the above, wherein said parameter is selected from a group consisting of: angel of image with respect to the object, spatial coordinates of the area of the image, location of MRI components and a combination thereof.

It is another object of the current invention to disclose an MRI system imaging a movable object as defined in any of the above, wherein said object is selected from a group consisting of: adult person, person under anesthesia, infant, premature baby, animal and a combination thereof.

It is another object of the current invention to disclose an MRI system imaging a movable object as defined in any of the above, wherein said at least one of said movement M is characterized by extent of said movement.

It is another object of the current invention to disclose an MRI system imaging a movable object as defined in any of the above, wherein said instruction are additionally for performing Fourier transformation on said consecutive image to momentum space (K-space) prior to said analysis.

It is another object of the current invention to disclose an MRI system imaging a movable object as defined in any of the above, wherein said analysis is performed on images in K-space.

BRIEF DESCRIPTION OF THE DRAWINGS

In order to understand the invention and to see how it may be implemented in practice, a few preferred embodiments will now be described, by way of non-limiting example only, with reference to be accompanying drawings, in which.

DETAILED DESCRIPTION OF THE INVENTION

The following description is provided so as to enable any person skilled in the art to make use of the invention and sets forth examples contemplated by the inventor of carrying out this invention. Various modifications, however, will remain apparent to those skilled in the art, since the generic principles of the present invention have been defined specifically. Also, it is to be understood that the phraseology and terminology employed herein is for the purpose of description and should not be regarded as limiting.

Figure 1:
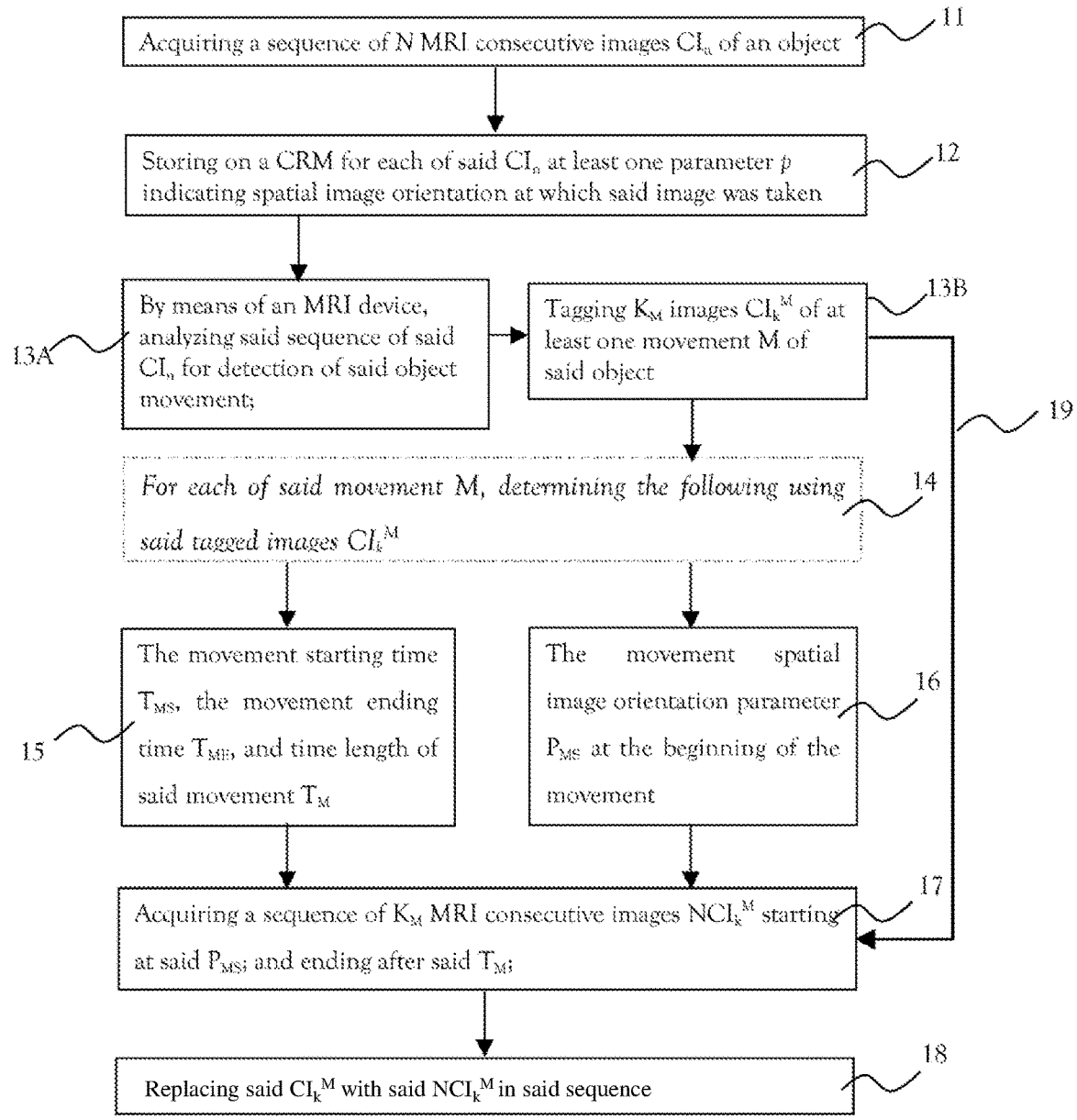
FIG. 1 illustrates a first method for reducing the effect of object movements along MRI imaging using an MRI-based motion detector.

According to one embodiment of the present invention, a first method for reducing the effect of object movements along MRI imaging is disclosed. Reference is now made to FIG. 1, presenting an embodiment, which is based on an MRI motion detector (See step 13A), of such a method which inter alia comprises the following steps: (a) acquiring a sequence of N MRI consecutive images $CI_n$ of an object (11); (b) storing on a computer readable medium (CRM) for each of said $CI_n$ (12): at least one parameter p indicating spatial image orientation at which said image was taken; (c) analyzing (13A) said sequence of said $CI_n$ for detection of said object movement; and tagging (13B) thereby $K_M$ images $CI_k^M$ of at least one movement M of said object; (d) for each of said movement M, determining (14) the following using said tagged images $CI_k^M$—two of the following: the movement starting time $T_{MS}$, the movement ending time $T_{ME}$, and time length (15) of said movement $T_M$; the movement spatial image orientation parameter (16) $P_{MS}$ at the beginning of the movement, wherein said method additionally comprising for each said M, whose $T_M$ is shorter from a predetermined time length PT, steps of (e) acquiring a sequence of $K_M$ MRI consecutive images $NCI_k^M$ (17) starting at said $P_{MS}$; and ending after said $T_M$; (f) replacing said $CI_k^M$ with said $NCI_k^M$, then replacing said sequence $CI_n$ the images that correspond in location to $CI_k^M$ with its respective $CI_k^M$ image; (g) repeating steps (c)-(f) (19) until no more movements whose $T_M$ is shorter than said PT can be detected; thereby, producing an image sequence with reduced object-movement in MRI imaging (18).

Figure 2:
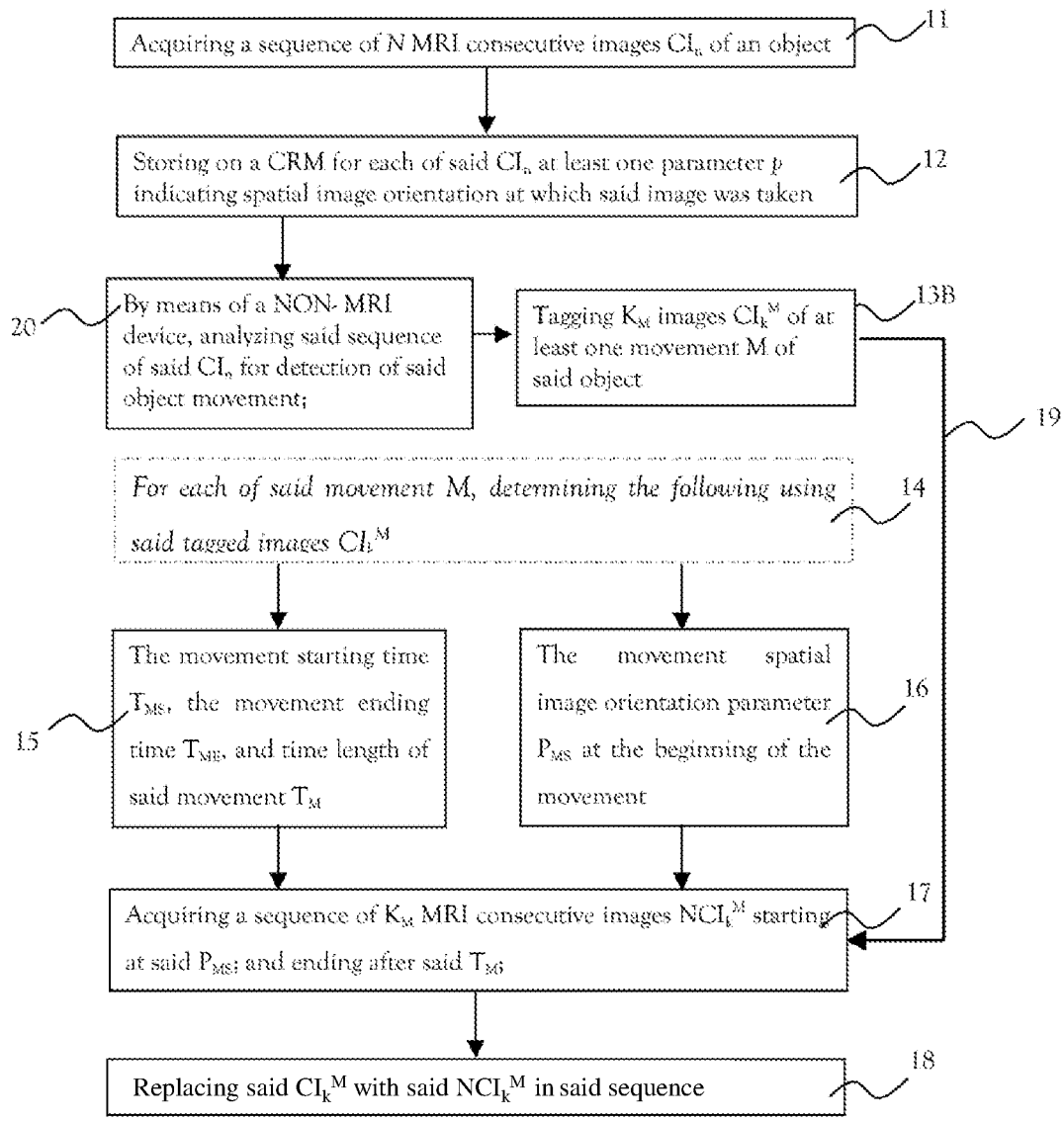
FIG. 2 illustrates a second method for reducing the effect of object movements along MRI imaging using a NON-MRI-based motion detector.

According to another embodiment of the present invention, a first method for reducing the effect of object movements along MRI imaging is disclosed. Reference is now made to FIG. 2, presenting an embodiment, based on a NON-MRI motion detector (See step 20), of such a method which inter alia comprises the following steps: (a) acquiring (11) a sequence of N MRI consecutive images $CI_n$ of an object; (b) storing on a computer readable medium (CRM) for each of said $CI_n$: at least one parameter p indicating spatial image orientation at which said image was taken; by means of one or more non-MRI motion detectors, (c) analyzing (20) motion of said object and tagging (13B) thereby $K_M$ images $CI_k^M$ of at least one movement M of said object; (d) for each of said movement M, determining (14) the following using said tagged images $CI_k^M$: two of the following: the movement starting time $T_{MS}$, the movement ending time $T_{ME}$, and time length (15) of said movement $T_M$; the movement spatial image orientation parameter $P_{MS}$ (16) at the beginning of the movement, wherein said method additionally comprising for each said M, whose $T_M$ is shorter from a predetermined time length PT, steps of (e) acquiring (17) a sequence of $K_M$ MRI consecutive images $NCI_k^M$ starting at said $P_{MS}$; and ending after said $T_M$; (f) replacing said $CI_k^M$ with said $NCI_k^M$, then replacing said sequence $CI_n$ the images that correspond in location to $CI_k^M$ with its respective $CI_k^M$ image; (g) repeating (19) steps (c)-(f) until no more movements whose $T_M$ is shorter than said PT can be detected; thereby, producing (18) an image sequence with reduced object-movement in MRI imaging.

Figure 3A:
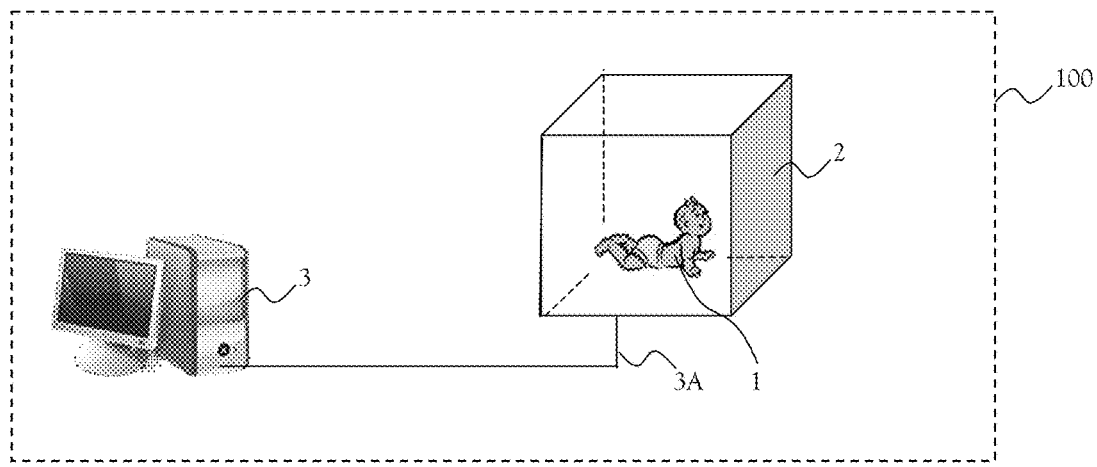
FIG. 3A illustrates in an out-of-scale manner a first system for reducing the effect of object movements along MRI imaging; the system comprises an MRI-based motion detector.

According to another embodiment of the present invention, a first MRI imaging system, adapted for reducing the effect of object movements along MRI imaging is disclosed. Reference is now made to FIG. 3A, presenting an embodiment of MRI imaging system (100), having an MRI-based motion detector, of such a system which inter alia comprises the following modules: an MRI device (2) adapted to take a sequence of N MRI consecutive images $CI_n$ of an object (1); each of said images is characterized by at least one parameter p indicating spatial image orientation at which said image was taken; a computer readable medium (CRM, 3) in communication (3A) with said MRI; said CRM having instructions thereon for executing a method comprising steps of: (i) analyzing said sequence of said $CI_n$; and tagging thereby $K_M$ images $CI_k^M$ of at least one movement M of said object; (ii) for each of said movement M, determining the following using said tagged images $CI_k^M$: (a) two of the following: the movement starting time $T_{MS}$, the movement ending time $T_{ME}$, and time length of said movement $T_M$; and (b) the movement spatial image orientation parameter $P_{MS}$ at the beginning of the movement; wherein for each said M, whose $T_M$ is shorter from a predetermined time length PT, said instructions are additionally adapted for (iii) acquiring a sequence of $K_M$ MRI consecutive images $NCI_k^M$ starting at said $P_{MS}$; and ending after said $T_M$; (iv) replacing said $CI_k^M$ with said $NCI_k^M$, then replacing said sequence $CI_n$ the images that correspond in location to $CI_k^M$ with its respective $CI_k^M$ image; and repeating steps (i)-(iv) until no more movements whose $T_M$ is shorter from said PT can be detected.

Figure 3B:
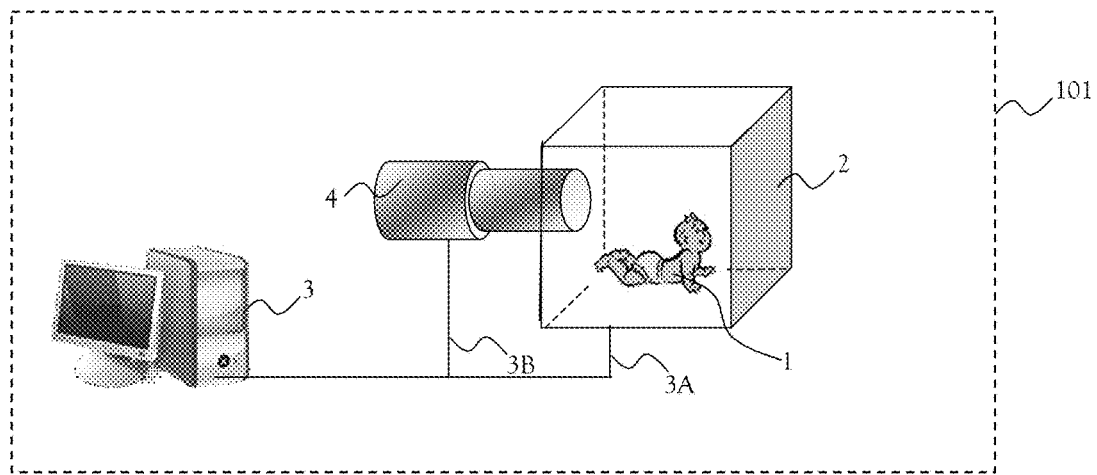
FIG. 3B illustrates in an out-of-scale manner a second system for reducing the effect of object movements along MRI imaging the system comprises a NON-MRI motion detector.

According to yet another embodiment of the present invention, a second MRI imaging system (101), adapted for reducing the effect of object movements along MRI imaging is disclosed. Reference is now made to FIG. 3B, presenting an embodiment of MRI imaging system (101), having a NON-MRI-based motion detector (See 4), of such a system which inter alia comprises the following modules: an MRI device (2) adapted to take a sequence of N MRI consecutive images $CI_n$ of an object (1); each of said images is characterized by at least one parameter p indicating spatial image orientation at which said image was taken; a computer readable medium (CRM, 3) in communication (3A) with said MRL MRI system 101 further comprises one or more NON-MRI motion detector (4) in communication (3B) with said CRM (3). CRM (3) having instructions thereon for executing a method comprising steps of: (f) analyzing said sequence of said $CI_n$; and tagging thereby $K_M$ images $CI_k^M$ of at least one movement M of said object; (ii) for each of said movement M, determining the following using said tagged images $CI_k^M$: (a) two of the following: the movement starting time $T_{MS}$, the movement ending time $T_{ME}$, and time length of said movement $T_M$; and (b) the movement spatial image orientation parameter $P_{MS}$ at the beginning of the movement; wherein for each said M, whose $T_M$ is shorter from a predetermined time length PT, said instructions are additionally adapted for (iii) acquiring a sequence of $K_M$ MRI consecutive images $NCI_k^M$ starting at said $P_{MS}$; and ending after said $T_M$; (iv) replacing said $CI_k^M$ with said $NCI_k^M$, then replacing said sequence $CI_n$ the images that correspond in location to $CI_k^M$ with its respective $CI_k^M$ image; and repeating steps (i)-(iv) until no more movements whose $T_M$ is shorter from said PT can be detected.

The MRI devices and methods as disclosed in any of the above are all targeted for avoiding or eliminating or otherwise reducing motion artifacts. These devises and methods are set useful for producing an image sequence characterized by reduced object-movement affect are all adapted to image uncontrollably movable objects, such as neonates, premature babies and laboratory animals; and especially to image motion-artifacts free images in relevant medical or research cases were restrain of the object is to be avoided (e.g., neonates clinical examination) or impossible (e.g., lab animals imaging for research).

The invention claimed is:

1. A method for reducing the effect of object movements along magnetic resonance imaging (MRI), the method comprising steps of:
   during MRI imaging of an object:
   a. acquiring a sequence, CI, of N consecutive MRI images where N is greater than 1, $CI_n$, of the object;
   b. for each of the N consecutive MRI images $CI_n$, storing on a computer readable medium (CRM) at least one parameter, p, indicating a spatial image orientation at which a respective MRI image of the N consecutive MRI images said image was taken;
   c. detecting movement of the object with one or more non-MRI motion detectors, and for each detected movement M analyzing the sequence CI to find a corresponding sequence $CI^M$ of $K_M$ images, $CI_k^M$, that were taken during said movement M;
   d. for each detected movement M, determining a starting time $T_{MS}$ of said movement, an ending time $T_{ME}$ of said movement, a time length $T_M$ of said movement, and a movement spatial image orientation parameter $P_{MS}$ at the beginning the movement;

e. for each detected movement M, whose $T_M$ is shorter than a predetermined time length PT:
  (i) acquiring a new sequence, $NCI_k^M$, of $K_M$ consecutive MRI images, $NCI_k^M$, starting at said $P_{MS}$ and
  (ii) replacing said sequence $CI_k^M$ with said $NCI_k^M$;
f. repeating steps (c)-(e) until no more movements whose $T_M$ is shorter than said PT can be detected to produce an image sequence with reduced object-movement.

2. The method according to claim 1, additionally comprising a step of selecting said non-MRI motion detectors from a group consisting of passive infrared sensors; detectors which sense body heat; mechanical detector; electronic detectors; optical detectors; acoustical detectors; sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

3. The method according to claim 1, wherein said parameter p is selected from a group consisting of: angle of the image with respect to the object, spatial coordinates of the area of the image, location of MRI components and a combination thereof.

4. The method according to claim 1, additionally comprising a step of selecting said object from a group consisting of: adult person, person under anesthesia, infant, premature baby, animal and a combination thereof.

5. The method according to claim 1, additionally comprising a step of characterizing at least one of said movement M by the extent of said movement.

6. The method according to claim 1, additionally comprising an image processing step prior to step (c); wherein said processing step comprising performing Fourier transformation on said consecutive images $CI_n$ to momentum space (K-space).

7. The method according to claim 6, wherein said analyzing is performed on images in K-space.

8. The method according to claim 1, wherein said object is selected from a group consisting of neonates, premature babies and laboratory animals.

9. The method according to claim 1, free of a step of restraining said object whilst imaging.

10. A magnetic resonance imaging (MRI) system imaging a movable object comprising:
  a. an MRI device adapted to take a sequence, CI, of N consecutive MRI images where N is greater than 1, $CI_n$, of an object;
  b. each of the N consecutive MRI images is characterized by at least one parameter p indicating a spatial image orientation at which a respective MRI image of the N consecutive MRI images was taken;
  c. a computer readable medium (CRM) in communication with said MRI device; said CRM having instructions thereon for executing a method comprising steps of: during MRI imaging of the object:
    i. detecting movement of the object with one or more non-MRI motion detectors, and, for each detected movement M analyzing the sequence to find a corresponding sequence $CI^M$ of $K_M$ images, $CI_k^M$, in which said movement M is detected,
    ii. for each detected movement M, determining a starting time $T_{MS}$ of said movement, an ending time $T_{ME}$ of said movement, a time length $T_M$ of said movement, and a movement spatial image orientation parameter $P_{MS}$ at the beginning the movement,
    iii. for each said M, whose $T_M$ is shorter than a predetermined time length PT:
      (a) acquiring a new sequence, $NCI_k^M$, of $K_M$ consecutive MRI images, $NCI_k^M$, starting at said $P_{MS}$, and
      (b) replacing said sequence $CI_k^M$ with said $NCI_k^M$;
    iv. repeating steps (i)-(iii) until no more movements whose $T_M$ is shorter from said PT can be detected to produce an image sequence with reduced object-movement.

11. The MRI system according to claim 10, wherein said MRI system additionally comprises a non-MRI motion detector.

12. The MRI system according to claim 11, wherein said non-MRI motion detectors are selected from a group consisting of: passive infrared sensors; detectors which sense body heat; mechanical detector; electronic detectors; optical detectors; acoustical detectors; sound detectors (acoustic sensors); opacity detectors (optical and infrared sensors and video image processors); geomagnetism detectors (magnetic sensors, magnetometers); reflection of transmitted energy detectors (infrared laser radar, ultrasonic sensors, and microwave radar sensors); electromagnetic induction detectors (inductive-loop detectors); vibration detectors (triboelectric, seismic, and inertia-switch sensors); and any combination thereof.

13. The system according to claim 10, wherein said parameter p is selected from a group consisting of: angle of the image with respect to the object, spatial coordinates of the area of the image, location of MRI components and a combination thereof.

14. The system according to claim 10, wherein said object is selected from a group consisting of: adult person, person under anesthesia, infant, premature baby, animal and a combination thereof.

15. The system according to claim 10, wherein at least one of said detected movements is characterized by extent of said movement.

16. The system according to claim 10, wherein said instruction are additionally for performing Fourier transformation on said consecutive images $CI_n$ to momentum space (K-space) prior to said analysis.

17. The system according to claim 16, wherein said analysis is performed on images in K-space.

18. The system according to claim 10, wherein said object is selected from a group consisting of neonates, premature babies and laboratory animals.

19. The system according to claim 10, wherein said object is not restrained along the imaging.

* * * * *